US012758759B2

(12) United States Patent
Richert et al.

(10) Patent No.: US 12,758,759 B2
(45) Date of Patent: Oct. 13, 2026

(54) FLUID PUMP

(71) Applicant: Berlin Heart GmbH, Berlin (DE)

(72) Inventors: Hendryk Richert, Berlin (DE); Oliver Peters, Berlin (DE)

(73) Assignee: Berlin Heart GmbH, Berlin (DE)

( * ) Notice: Subject to any disclaimer, the term of this patent is extended or adjusted under 35 U.S.C. 154(b) by 658 days.

(21) Appl. No.: 18/182,585

(22) Filed: Mar. 13, 2023

(65) Prior Publication Data

US 2023/0321427 A1 Oct. 12, 2023

(30) Foreign Application Priority Data

Mar. 13, 2022 (EP) .................................... 22161748

(51) Int. Cl.

| | |
|---|---|
| ***A61M 60/416*** | (2021.01) |
| ***A61M 60/221*** | (2021.01) |
| ***A61M 60/237*** | (2021.01) |
| ***A61M 60/405*** | (2021.01) |
| ***A61M 60/82*** | (2021.01) |

(Continued)

(52) U.S. Cl.

CPC ........ *A61M 60/416* (2021.01); *A61M 60/221* (2021.01); *A61M 60/237* (2021.01); *A61M 60/405* (2021.01); *A61M 60/82* (2021.01); *A61M 60/825* (2021.01); *F04D 3/005* (2013.01); *F04D 29/0467* (2013.01)

(58) Field of Classification Search

CPC ............... F04D 29/0467; F04D 29/181; F04D 13/0633; F04D 3/005; A61M 60/405; A61M 60/92; A61M 60/825; A61M 60/221; A61M 60/237

See application file for complete search history.

(56) References Cited

U.S. PATENT DOCUMENTS 3,553,807 A * 1/1971 Laing .................... F04D 13/026 29/441.1
3,732,445 A * 5/1973 Laing .................... F04D 13/026 310/90

(Continued)

FOREIGN PATENT DOCUMENTS

| | | |
|---|---|---|
| DE | 1 797 546 | 4/1972 |
| DE | 2 246 418 | 5/1973 |
| DE | 20 2006 013 239 U1 | 2/2007 |

OTHER PUBLICATIONS

European Search Report for European Patent Application No. 22161748.3, dated Sep. 7, 2022 (8 pp.).

*Primary Examiner* — Kenneth J Hansen
(74) *Attorney, Agent, or Firm* — Crowell & Moring LLP

(57) ABSTRACT

A fluid pump conveys a fluid, such as blood. A fluid channel that is bounded by a channel wall and a rotor arranged in the fluid channel and that is rotatably mounted about a pivot point of the bearing with a mechanical, hydrodynamic and/or hydrostatic, axial and radial bearing. The fluid channel has a spherical section and the rotor has a rotor body and a conveying element that is arranged within the spherical section of the fluid channel and configured to generate a substantially spherical rotational area of the rotor. The spherical center of the spherical section of the fluid channel and the spherical center of the spherical rotational area substantially coincide with the pivot point so that a minimum distance between the rotor and the channel wall is maintained in the spherical section upon a tilting of the rotor.

18 Claims, 13 Drawing Sheets

(51) Int. Cl.

| | |
|---|---|
| ***A61M 60/825*** | (2021.01) |
| ***F04D 3/00*** | (2006.01) |
| ***F04D 29/046*** | (2006.01) |

(56) References Cited

U.S. PATENT DOCUMENTS

| | | | | |
|---|---|---|---|---|
| 3,803,432 | A * | 4/1974 | Laing | H02K 17/12<br>310/90 |
| 4,730,989 | A | 3/1988 | Laing | |
| 2007/0286754 | A1 * | 12/2007 | Laing | F04D 29/628<br>29/888.02 |
| 2014/0255225 | A1 * | 9/2014 | Aber | A61M 60/825<br>417/420 |

* cited by examiner

FLUID PUMP

PRIORITY

This application claims priority to EP Patent Application No. 22161748.3 filed on Mar. 13, 2022, entitled "FLUID PUMP". The entire disclosure of the above application is incorporated herein by reference.

TECHNICAL FIELD

The embodiments relate to a fluid pump for conveying a fluid, such as blood.

BACKGROUND

Blood pumps are made in different configurations. Rotors of mechanically mounted blood pumps are usually held at the front and rear sides by ball cup bearings. An axial gap of a few micrometers in the bearings permits a free rotation with a good axial guidance. Blood can diffuse into the bearings in principle. These bearings correspond to two spaced apart fixed bearings in mechanics.

There is a risk due to the deposition of proteins in the open bearing gap that substantial axial forces arise in this bearing. Even with small coefficients of friction, the increased axial force results in increased friction power that may result in coagulation of the biological components in and around the bearing, which results in a worse coefficient of friction in poor heat removal into the blood. A failure of the bearings and thus of the pumps is then a question of time. These pump types are only pursued in isolated cases due to the poor command of the mechanical bearings, in particular due to unpredictable thrombogenicity, that is very largely not understood, also due to said effect.

A further form of mechanical mounting is represented by a cone bearing mounting, wherein the mechanical bearing can be axially flushed through. However, deposition in the gap here also results in an increase in the coefficient of friction with the already mentioned potential consequences.

Another direction of development dealt with hydrodynamically mounted pumps. Here, blood is used as a lubricant and as a suspension element. The increased shearing load of the blood in the gap is evidently well tolerated thereby. These systems appear to work well at low hemolysis, but have very largely ceased to be used due to the slightly increased thrombogenicity. The advantages of all these pumps consists of a very simple control since only the rotor has to be driven. A standardized back EMF motor controller that evaluates the induction in the motor coils is sufficient for normal operation. Electronics in the pump can thereby be dispensed with and three lines have to be present in the driveline as a minimum.

There are, on the other hand, fully magnetically mounted pumps. The complete control of the rotor position by magnetic forces characterizes this pump generation and enables a contactless suspension of a rotor in the flow channel. Extensive control electronics are, however, required in the pump for this purpose. The driveline of such pumps typically has a large diameter and has very little flexibility. If the control electronics for the active magnetic bearing is integrated in the pump, the driveline can admittedly manage with fewer lines. The pump base is enlarged, however, which can result in a problem for smaller patients.

There as passively magnetically mounted pumps as intermediate solutions with potential for the implantable sector. The rotor here, for example, is axially mechanically mounted at the front side and is radially mechanically fettered at the front and outlet sides. The control of the rotor is restricted to the rotation of the rotor as with the mechanically mounted pumps. The mechanical mounting consists of a purely axial mounting so that the rotor is radially deflected in that it follows the radially active forces corresponding to the bearing stiffness, i.e. the rotor moves on a cycloidal path around the axis of symmetry of the radial magnetic mounting of the pump.

Since the forces primarily attack the blades in the volute, the rotor may tilt so that the axial support surface is reduced. In this long-term, this results in partial wear (increase in roughness) of the surface in the region of the area swept over by the rotor bearing. In addition, blood can penetrate into the tilted mechanical bearing and can be activated, i.e. crushed, there, which may create a thrombogenic danger zone. Axially bladed, magnetically passively mounted blood pumps have the disadvantage that the blade gap always has to be large due to the return properties of the magnetic bearings, whereby the blade losses in this pump type are intrinsically increased.

SUMMARY

Pumps that can dispense with the rotor bearing regulation tend to be better suited for miniaturization, contain fewer components, thereby have a simpler design, that is can be made more robustly and considerably smaller than a fully magnetic system.

An axial pump may convey worse in the low flow range if the radial gap becomes too large since the gap losses (the flowing over of the blade edges against the main direction of flow) increase disproportionately. The management of a lack of damping in passive magnetic bearings may be critical, with lack of damping having the result that periodic excitations of small amplitude in the vicinity of resonance can lead to large deflections of the rotors (in the millimeter range). Resonance may be present in the working range of the blood pumps since the speed depends on the patient. Blades can produce damage to the wall on contact and can thus facilitate increased blood damage or germ formation for thrombus growth.

An axial fluid pump that solves these issues is described in the following embodiments. It is an object of the embodiments to provide an axial fluid pump that is efficient, robust, and safe with respect to radial tilting of the rotor and that allows miniaturization. The above-described object is achieved by a fluid pump in accordance with the embodiments and claims.

A fluid pump in accordance with the embodiments for conveying a fluid, in particular blood, comprises a fluid channel that is bounded by a channel wall, a rotor that is arranged in the fluid channel and that is rotatably mounted about a pivot point of the bearing by means of a mechanical, hydrodynamic, and/or hydrostatic axial and radial bearing, wherein the fluid channel has a spherical section, the rotor has a rotor body and a conveying element that is arranged within the spherical section of the fluid channel and that is suitable to generate an at least regionally substantially spherical rotational area of the rotor, and wherein the spherical center of the spherical section of the fluid channel and the spherical center of the spherical rotational area substantially coincide with the pivot point so that a minimal/minimum spacing between the rotor and the channel wall in the spherical section is constant on a tilting of the rotor.

The rotor can tilt a great amount out of its nominal position without any contact between the rotor and the fluid channel being able to occur due to the spherical arrangement of the spherical section of the fluid channel and the conveying element. In this case, the minimal/minimum distance between the rotor and the channel wall of the fluid channel can be ideally set. Any contact between the rotor and the channel wall is avoided by the above-described spherical design and arrangement of the fluid channel and the rotor so that additional measures such as the use of a safety bearing can be dispensed with. The fluid pump can thereby have a simple, compact, and safe design.

The fluid channel can be designed as hollow cylindrical and substantially rotationally symmetrical about an axis of rotation. The fluid substantially flows in a longitudinal direction that corresponds to a direction along the axis of rotation. The spherical section of the fluid channel is located in the region or in the vicinity of the bearing. The bearing in particular overlaps the spherical section in the longitudinal direction or is arranged adjacent to, in particular directly adjacent to, the spherical section.

A spherical hydrodynamic mounting provides the advantage that the mounting permits a tilting of the rotor without impairing the bearing effect.

In accordance with an embodiment, the bearing can be a ball cup bearing or a pin bearing, in particular a pin on blind hole bearing.

In accordance with another embodiment, the fluid pump can further comprise a passively magnetic bearing, with the passively magnetic bearing being formed as a rocker bearing for returning or bounding a tilt of the rotor and/or being configured to axially preload the rotor with respect to the fluid channel. Too strong a pressing of the rotor into the bearing and the arising of friction losses there can be prevented by the preload. In addition, an ideal bearing gap into which the fluid, in particular blood, to be conveyed cannot flow can be set by means of the magnetic preload. The magnetic preload can likewise be used to press the rotor into the bearing in every operating state.

In accordance with another embodiment, the fluid pump can further comprise a motor stator arranged at the channel wall of the fluid channel and a motor magnet integrated in the rotor body or in the conveying element, with a passively magnetic rocker mounting being implemented by a magnetic attraction or repulsion between the motor stator and the motor magnet.

In accordance with another embodiment, the fluid channel can be shaped as conical, tapering toward the bearing, on a side disposed opposite the bearing, with a taper angle of the fluid channel corresponding to a maximum tilt angle of the rotor within the fluid channel. A conical tapering of the fluid channel toward the bearing permits a nestling of the rotor at the fluid channel and prevents contact with or damage to the rotor body on a large radial tilt of the rotor.

In accordance with another embodiment, the rotor body can be shaped as conical, tapering in a direction away from the bearing, on a side disposed opposite the bearing, with a taper angle of the rotor body corresponding to a maximum tilt angle of the rotor within the fluid channel. A conical tapering of the rotor toward the inlet region permits a nestling of the rotor at the fluid channel and prevents contact with or damage to the rotor body in the inlet region on a large radial tilt of the rotor. The conical tapering of the rotor can form a large-area hydrodynamic bearing with the fluid channel, said bearing being able to prevent a contact between the rotor and the fluid channel, also with tilting effects greater than the maximum tilting effect of the passive magnetic bearing or motor stator.

In accordance with another embodiment, the fluid pump can further comprise a hydrostatic or hydrodynamic auxiliary bearing arranged in the fluid channel to bound the tilting of the rotor.

In accordance with another embodiment, the hydrostatic or hydrodynamic auxiliary bearing can be formed by guide blades arranged at the channel wall.

In accordance with another embodiment, hydrodynamically active elements can be arranged on a side of the fluid channel disposed opposite the bearing at the channel wall and/or at the rotor to improve a nestling of the rotor at the channel wall on a tilting of the rotor.

In accordance with another embodiment, the fluid channel can have a fluid inlet and a fluid outlet and the bearing can be arranged at the fluid inlet, at the fluid outlet, or at a center of the fluid channel.

In accordance with another embodiment, the fluid channel can further have an axial, tangential, or axially tangentially mixed fluid outlet.

In accordance with another embodiment, the fluid channel can comprise a fluid outlet and the fluid pump can have a volute in the region of the fluid outlet, in particular a ring volute, a logarithmic volute, and/or a volute having an axial portion.

In accordance with another embodiment, the mechanical bearing can comprise or consist of a hemocompatible, hard, wear resistant, and/or thermally conductive material, in particular a ceramic material, in particular aluminum oxide ($Al_2O_3$), silicon carbide (SiC), zirconium oxide ($ZrO_2$) or silicon nitride ($Si_3N_4$), a mixed ceramic material, in particular $Al_2O_3$/SiC, aluminum reinforced zirconium oxide (ATZ), or zirconium oxide reinforced aluminum oxide (ZTA), crystalline, in particular diamond, sapphire, ruby, or quartz, or tantalum nitride, in particular a tantalum nitride thin film, and/or can comprise a sliding layer, in particular diamond-like carbon (DLC), SiN, or tungsten carbide/carbon (WC/C).

In accordance with another embodiment, the bearing can be axially mechanically displaceable to set an ideal distance between the fluid channel and the conveying element.

In accordance with another embodiment, the bearing can be axially mechanically displaceable by means of a thread before the putting into operation of the fluid pump.

In accordance with another embodiment, the magnetic bearing and/or the motor stator can be axially displaceable so that the preload of the rotor in the bearing can be set.

In accordance with another embodiment, motor or bearing magnets can be arranged below the spherical rotational area of the rotor.

In accordance with another embodiment, the magnets can form a closed or interrupted ring that connects the conveying elements.

In accordance with one embodiment, a fluid pump having an at least partially spherical fluid channel in the region of the bearing and of the conveying elements thus results in a solution in which the rotor is axially fixed at a point and is radially fixed with the aid of a single mechanical ball cup bearing or with the aid of a hydrodynamic or hydrostatic bearing. The remaining three degrees of freedom (rotation or tilting about two axes) are controlled by magnetic forces. The rotation about the axis of rotation is determined by a motor. The tilt degrees of freedom are fettered passively by (i) an additional magnetic bearing or (ii) the interaction between the motor magnet and the motor stator. The rotor can tilt a great amount out of its nominal position without any contact between the conveying element and the fluid channel being able to occur due to this spherical arrangement. The gap between the conveying element and the channel wall can be set to the ideal amount in a technical flow aspect since the rotor is precisely mechanically or hydraulically mounted in the three geometrically decisive degrees of freedom. Losses of the conveying elements are minimized and retrograde flow through the pump is avoided due to the steep characteristic. The magnetically preloaded mechanical bearing cannot result in an increase in friction power due to axial tensioning toward a second, unyielding mechanical bearing so that the bearing loss power permanently remains at a low level. The coagulation of blood components is thus avoided and the bearing remains functional in the long term. The increased permitted tilt range of the rotor is advantageous for the magnetic bearing since the fluid damping that is too low with axial pumps is now sufficient to prevent a contact between the rotor and the channel wall. The design with a supporting ring magnet bearing enables an optimum flushing through the fluid pump with only small secondary flow portions in the region of the mechanical bearing. The design generally permits a front-side or rear-side mechanical bearing, with the combination of the bearing at the outlet side with a volute being able to be particularly advantageous. A hydrodynamic or hydrostatic mounting equally appears possible. The motor and the bearing magnets can be accommodated in the rotor body, but also in the conveying elements, or in an outer sphere.

The proposed fluid pump design provides the advantages that a secondary flow (going beyond the edges of the conveying elements) is prevented, that the motor driver and thus the control unit is simple since no active bearing regulation is required, and that the motor as a heat source can be cooled in the accelerated main flow. A safety bearing is furthermore no longer necessary since the rotor can defect freely up to a potential sliding on of the rotor, in particular with the conical design of the rotor, onto the channel wall. The characteristic of the fluid pump can be set particularly simply and the mechanical bearing components can be desired particularly simply limited in load and flow. The corresponding advantage with respect to the running stability is that the turbulences downstream of the conveying elements do not impact on a rotor and thus cannot excite them to oscillate.

BRIEF DESCRIPTION OF THE DRAWINGS

The embodiments of a fluid pump will be described in more detail with reference to Figures, which illustrate examples of those embodiments. The same or different reference numerals may be used for the same or similar elements in the Figures and their explanation may be omitted in part. Non-limiting and non-exhaustive embodiments are described with reference to the following drawings. The components in the drawings are not necessarily to scale, emphasis instead being placed upon illustrating the principles of the invention. The drawings, like referenced numerals, designate corresponding parts throughout the different views.

DETAILED DESCRIPTION

Figure 1:
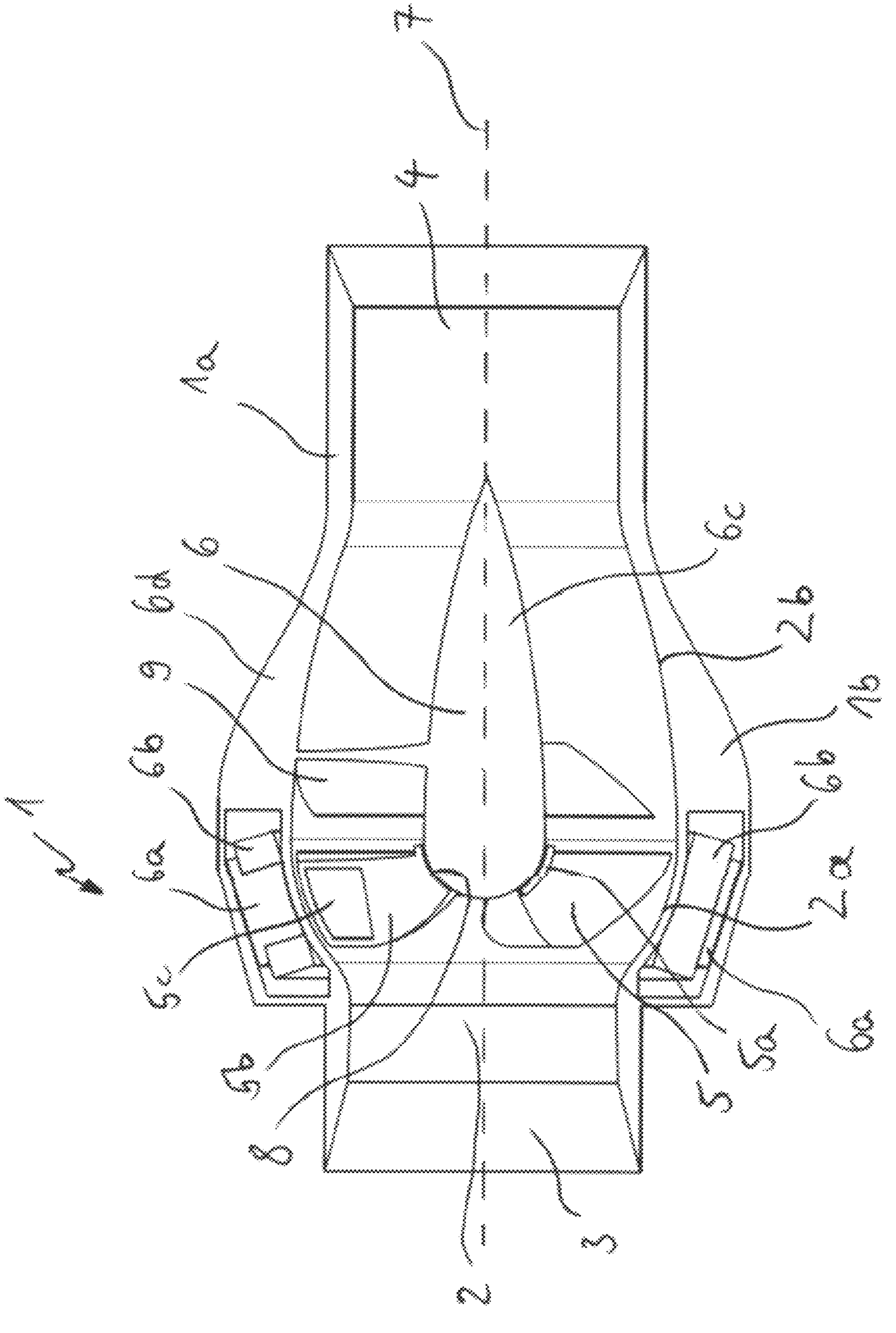
FIG. 1 is a blood pump mounted at the inlet side in accordance with a first embodiment.

FIG. 1 shows a blood pump 1 in accordance with a first embodiment in a longitudinal sectional view. The blood pump 1 has a substantially hollow cylindrical pump housing 1*a* that is substantially rotationally symmetrical about an axis of rotation 7. The pump housing 1*a* has a spherical widening 1*b* in a middle region of the pump housing 1*a*. The blood pump 1 has a fluid channel 2 that is bounded by a channel wall 2*b* of the fluid pump 1 in an inner region of the pump housing 1*a*. The fluid channel 2 extends in an axial direction from an inlet region 3 to an outlet region 4. The spherical widening 1*b* is located between the inlet region 3 and the outlet region 4.

The fluid channel 2 has a spherical section 2*a* in the region of the spherical widening 1*b*. The blood pump 1 furthermore has a rotor 5 and a stator 6 in this region. The stator 6 comprises a drop-like element 6*c* that is arranged in a streamlined manner along the axis of rotation 7 in the fluid channel 2. The pump housing 1*a* is furthermore part of the stator 6. The drop-like element 6*c* is fixedly connected to the pump housing 1*a* via guide blades 9 that are likewise parts of the stator 6. In the pump housing 1*a*, a plurality of stator irons 6*a* are arranged in ring shape around the fluid channel 2 in the region of the widening 1*b*. The stator irons 6*a* are each surrounded by stator windings 6*b* in parallel with the channel wall 2*b*.

The front end of the drop-like element 6*c* at the inlet side forms an axially flushable mechanical ball cup bearing 8 for the rotor 5. The rotor 5 is rotatably mounted about the axis of rotation 7 radially and axially mechanically on the drop-like element 6*c* of the stator 6. The rotor 5 is held on the drop-like element 6*c* by a small rotor body 5*a*. The rotor body 5*a* rigidly connects conveying elements 5*b* to one another that make up a main portion of the rotor 5.

Permanent magnets 5*c* are integrated in the conveying elements 5*b* in an outer region of the conveying elements 5*b* disposed toward the channel wall 2*b*. The stator irons 6*a* and associated stator windings 6*b* form a plurality of electromagnetics that cooperate with the permanent magnets 5*c* to drive the rotor 5. The electromagnets 6*a*, 6*b* of the stator 6 together with the permanent magnets 5*c* of the rotor 5 serve a passive return of the rotor 5 on a tilting of the rotor 5 in the direction of the channel wall 2*b* and thus serve a fixing of the remaining two tilt degrees of freedom of the rotor 5.

A shape of the conveying elements 5*b* is furthermore adapted to a spherical curvature of the channel wall 2*b* on outer sides disposed toward the channel wall 2*b* so that the conveying elements 5*b* sweep over a spherical rotational area on a rotation of the rotor 5. The location of the rotor 5 in the fluid channel 2 and the position of the spherical portion 2a are furthermore aligned with one another such that the center of the spherical rotational area of the conveying elements 5b or of the rotor 5 and the center of the spherical section 2a of the fluid channel 2 substantially coincide with the swivel point of the bearing 8. A minimal or minimum distance between the conveying elements 5b or the rotor 5 and the channel wall 2b thereby also remains substantially constant on a tilting of the rotor 5 toward the channel wall 2b. A contact of the rotor 5 with the channel wall 2b and possible damage to the rotor 5 and impairment of the function of the blood pump 1 associated therewith are thereby prevented.

The conveying elements 5b serve the conveying of the blood to be conveyed by the blood pump 1 from the inlet region 3 to the outlet region 4 and are designed such that a conveying is made possible in a mixed radial and axial direction. The guide blades 9, in addition to the conveying elements 5b, provide an efficient conveying of the blood to the outlet 4 of the blood pump 1.

Figure 2:
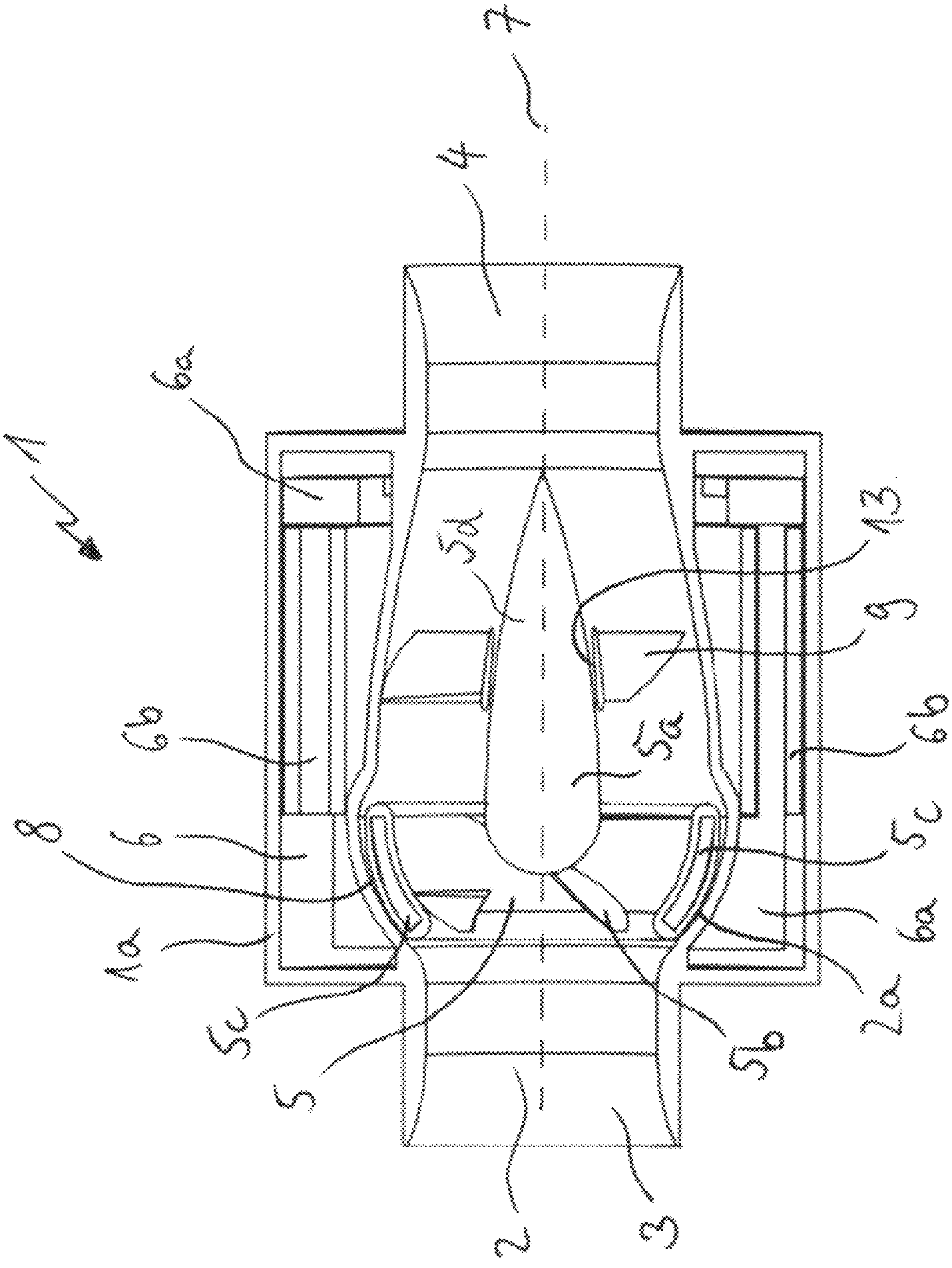
FIG. 2 is a blood pump mounted at the inlet side in accordance with a second embodiment.

FIG. 2 shows a blood pump 1 in accordance with a second embodiment in a longitudinal sectional view. The blood pump 1 has a pump housing 1a having an inlet region 3 for the blood and an outlet region 4 for the blood. The pump housing 1a is substantially rotationally symmetrical with an axis of rotation 7. A fluid channel 2 that is bounded by a channel wall 2b leads through the pump housing 1a in an axial direction. The fluid channel 2 has a substantially drop-like shape between the inlet region 3 and the outlet region 4. The fluid channel 2 initially has a spherical section 2a downstream of the inlet region 3 before the fluid channel 2 tapers in the direction of the outlet region 4. A rotor 5 having a rotor body 5a is arranged in the drop-like region of the fluid channel 2. In the front region of the rotor 5 facing the inlet region 3, the rotor body 5a is designed in ring shape and is connected via conveying elements 5b to a drop-like element 5d that is part of the rotor body 5a. The drop-like element 5d tapers acutely toward the outlet region 4. A plurality of permanent magnets 5c are arranged in the ring-shaped region. The rotor 5 is radially and axially hydrodynamically or hydrostatically mounted in the spherical section 2a, with the channel wall 2b representing the hydrodynamic or hydrostatic bearing 8 in the spherical section. The drop-like element 5d of the rotor 5 is furthermore radially mounted by means of a ring-shaped hydrodynamic or hydrostatic bearing 13, with the hydrodynamic or hydrostatic bearing 13 being rigidly connected to the pump housing 1a via guide blades 9. The bearing 8 fixes the ring-shaped region of the rotor 5 in the axial and radial directions. The bearing 13 fixes the drop-like element 5d of the rotor 5 in the radial direction.

The blood pump 1 is equipped with a bearing-less motor stator to drive the rotor 5. A plurality of stator irons 6a are arranged around the drop-like region of the fluid channel 2 in the pump housing 1a. The stator irons 6a are wound around by stator windings 6b in the region of the tapering fluid channel 2 perpendicular to the channel wall 2b. The stator irons 6a contact the outer side of the spherical fluid channel in the region of the spherical section 2a. The stator irons 6a with stator windings 6b form electromagnets that cooperate with the permanent magnets 5c to drive the rotor 5.

In the spherical section 2a of the fluid channel 2, the ring-shaped region of the rotor 5 is likewise spherically shaped on the outer side disposed toward the channel wall 2b and is adapted to a curvature of the channel wall 2b. The center of the spherical curvature of the outer side of the ring-shaped region of the rotor 5 and the center of the spherical curvature of the spherical section 2a substantially coincide with the pivot point of the bearing 8 so that the minimal/minimum distance between the ring-shaped region of the rotor 5 and the channel wall 2b is also substantially constant on a tilting of the rotor 5. A contact of the rotor 5 with the channel wall 2b and possible damage to the rotor 5 and impairment of the function of the blood pump 1 associated therewith are thereby prevented.

The conveying elements 5b serve the conveying of the blood to be conveyed by the blood pump 1 from the inlet region 3 to the outlet region 4 and are designed such that a conveying is made possible in a mixed radial and axial direction. The guide blades 9 arranged downstream, in addition to the conveying elements 5b, provide an efficient conveying of the blood to the outlet of the blood pump 1.

The cooperation of the rotor magnets 5c and the motor stator 6a, 6b passively bounds a radial tilt of the rotor 5. A preload of the rotor 5 can additionally be set toward the outlet region 4 by the rotor magnets 5c and the motor stator 6a, 6b.

Figure 3:
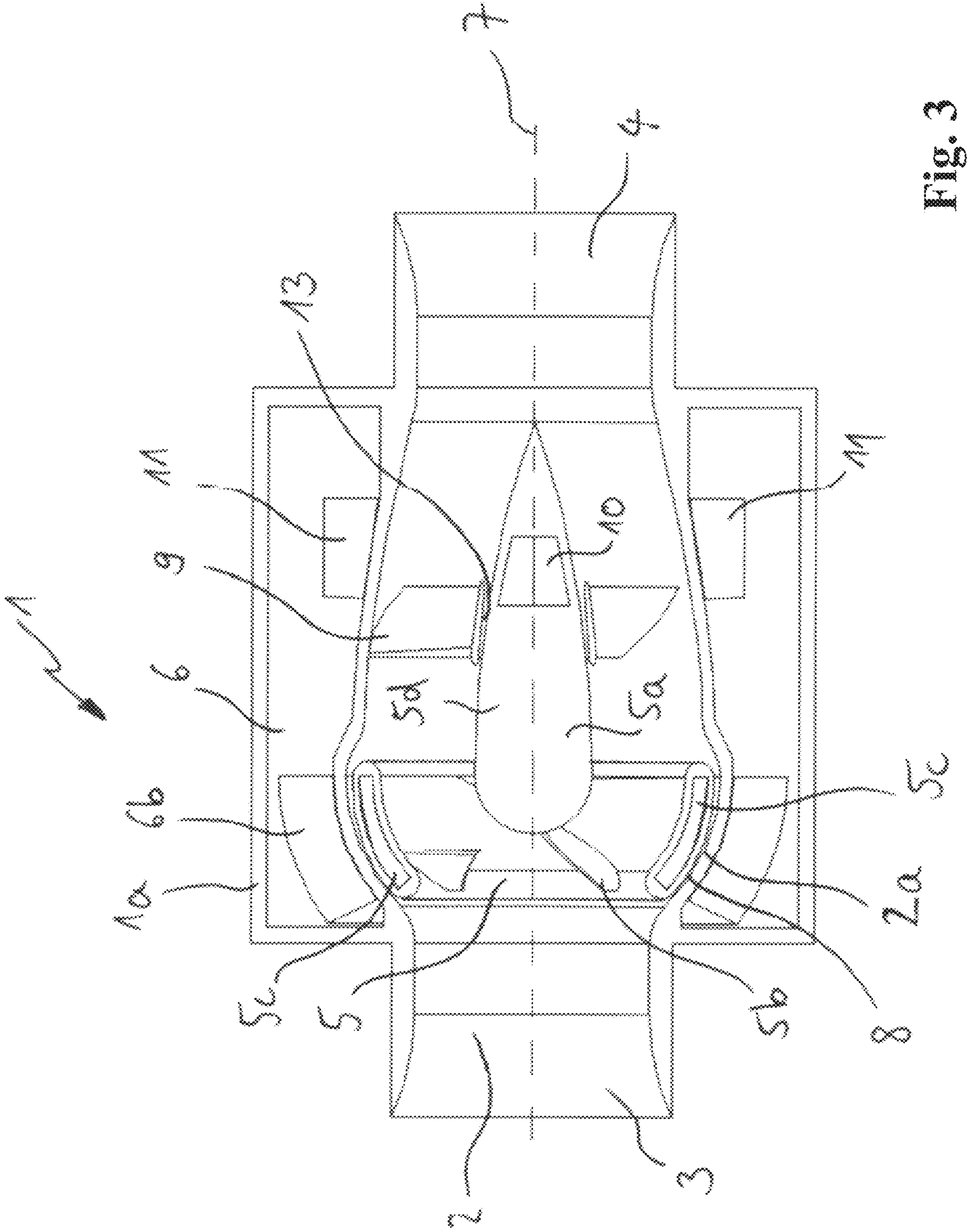
FIG. 3 is a blood pump mounted at the inlet side in accordance with a third embodiment.

FIG. 3 shows a blood pump 1 in accordance with a third embodiment in a longitudinal sectional view. The blood pump 1 is similar to the blood pump of FIG. 2 except for the design of the motor stator 6b and an additional passive magnetic stator rocker bearing 11. The motor stator 6b is free of irons. The additional magnetic stator rocker bearing 11 is located in the rear region of the blood pump 1 facing the outlet region 4 and cooperates with the rotor magnets 10 that are arranged in the drop-like element 5d of the rotor 5. The stator rocker bearing 11 is radially repelling and thus holds the drop-like element 5d centrally in the fluid channel 2, with remaining tilt degrees of freedom being stabilized.

The further illustrated features of the blood pump 1 agree with the blood pump of FIG. 2. In the spherical section 2a of the fluid channel 2, the ring-shaped region of the rotor 5 is likewise spherically shaped on the outer side disposed toward the channel wall 2b and sweeps over a spherical rotational area on a rotation of the rotor 5. A curvature of the outer side of the ring-shaped region of the rotor 5 is adapted to a curvature of the channel wall 2b. The center of the spherical curvature of the outer side of the ring-shaped region of the rotor 5 and the center of the spherical curvature of the spherical section 2a substantially coincide with the pivot point of the bearing 8 so that the minimal/minimum distance between the ring-shaped region of the rotor 5 and the channel wall 2b is also substantially constant on a tilting of the rotor 5. A contact of the rotor 5 with the channel wall 2b and possible damage to the rotor 5 and impairment of the function of the blood pump 1 associated therewith are thereby prevented.

Figure 4:
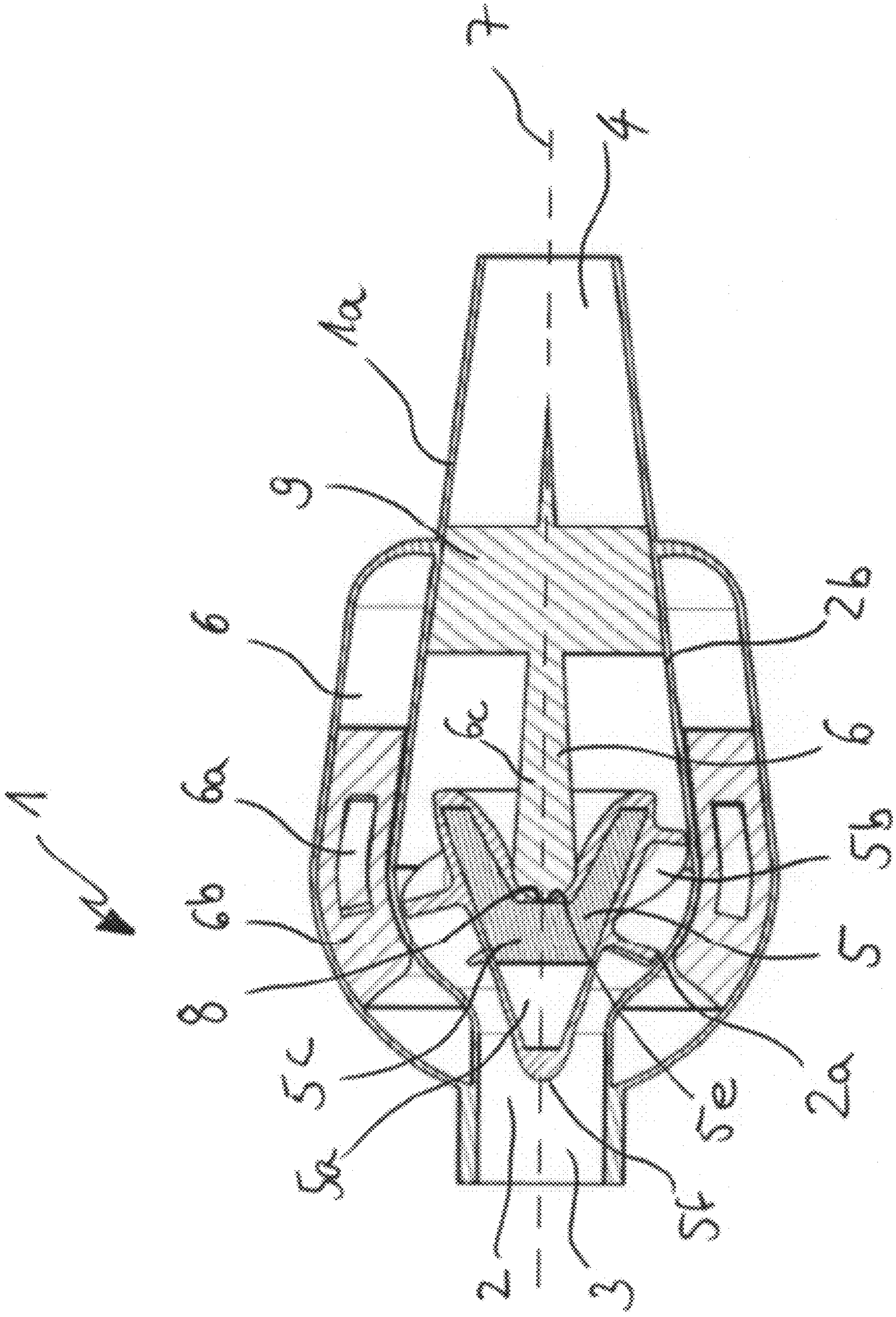
FIG. 4 is a blood pump mounted at the inlet side in accordance with a fourth embodiment.

FIG. 4 shows a blood pump 1 in accordance with a fourth embodiment in a longitudinal sectional view. The blood pump 1 is similar in principle to the blood pump of FIG. 1. The hollow cylindrical pump housing 1a has an inlet region 3 and an outlet region 4 for the blood. A fluid channel 2 that is bounded by a channel wall 2b leads between the inlet region 3 and the outlet region 4. The fluid channel 2 has a spherical section 2a downstream of the inlet region 2 and tapers in drop form toward the outlet region 4.

The blood pump 1 substantially differs from the blood pump of FIG. 1 in the form of the rotor 5. The rotor body 5a of the rotor 5 has a conical shape that has a cutout 5e at the side facing the drop-like element 6c of the stator 6. The drop-like element 6c of the stator 6 engages into this cutout 5e and thus forms the axial and radial mechanical ball cup bearing 8 for the rotor 5. The rotor body 5a is positioned in the flow channel 2 such that a tip 5*f* of the conical shape of the rotor body 5*a* projects into the inlet region 3 downstream of the spherical section. A large part of a jacket surface of the conical shape lies in the spherical section 2*a* of the fluid channel 2 and extends quasi in parallel with the channel wall 2*b*.

Conveying elements 5*b* that convey the blood from the inlet region 3 in the direction of the outlet region 4 in a mixed radial and axial direction are arranged in the spherical region on the jacket surface of the rotor body 5*a*. The conveying elements 5*b* are arranged on the jacket surface and are shaped such that they sweep over a spherical rotational area on a rotation of the rotor 5. The conveying elements 5*b* are furthermore shaped and are positioned in the fluid channel 2 such that the center of the spherical rotational area and the center of the spherical section 2*a* of the fluid channel 2 substantially coincide with the pivot point of the bearing 8. This embodiment of the rotor 5 and the fluid channel 2 makes it possible that a minimal/minimum distance between the rotor 5 and the channel wall 2*b* also remains constant on a tilting of the rotor 5 and prevents the rotor 5 from contacting the channel wall 2*b* and the arising of damage to the rotor 5 or to the channel wall 2*b* or the impairment of the function of the blood pump 1 on the tilting of the rotor 5.

The blood pump 1 in a similar manner to the blood pump of FIG. 1 has guide blades 9 that are arranged downstream of the rotor 5 and that rigidly connect the drop-like element 6*c* to the pump housing 1*a*. The guide blades 9 support and improve a flow of the blood to the outlet region 4. Flushing bores for flushing the mechanical bearing that may be necessary are not shown, but can easily be introduced into the rotor.

Figure 5:
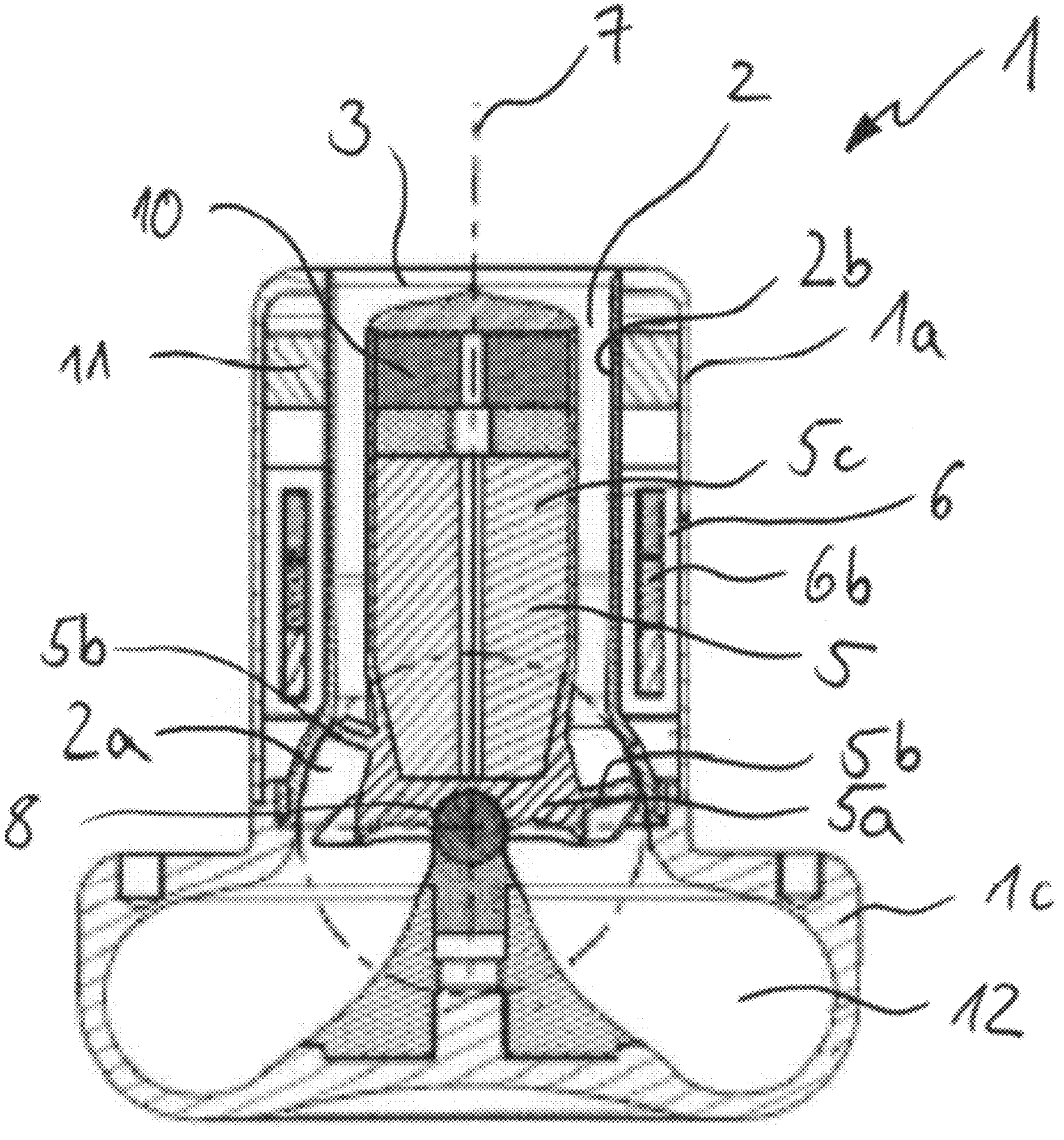
FIG. 5 is a blood pump mounted at the outlet side in accordance with a fifth embodiment.
Figure 6:
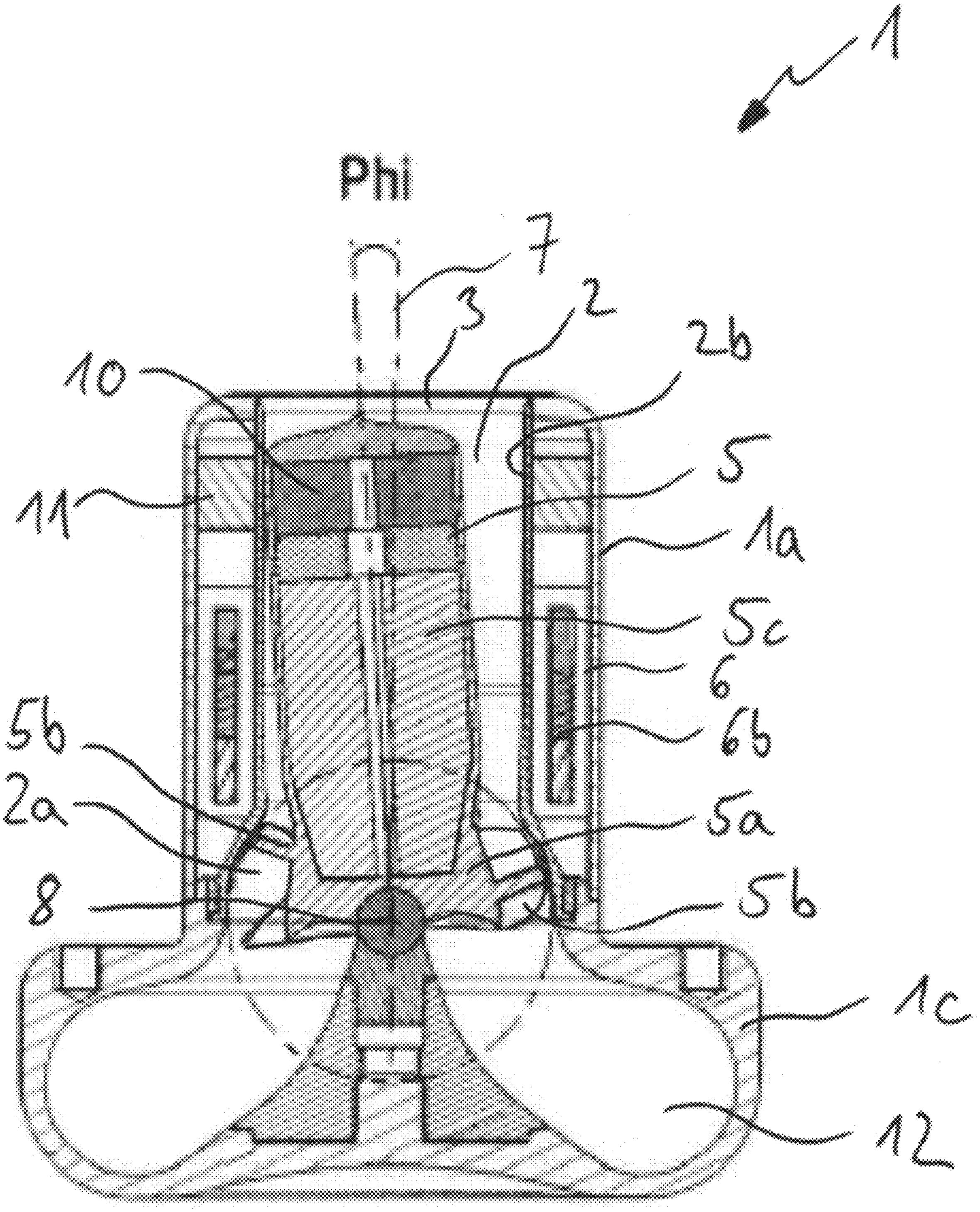
FIG. 6 is the blood pump mounted at the outlet side in accordance with FIG. 5 with a rotor tilt.

FIGS. 5 and 6 show a blood pump 1 in accordance with a fifth embodiment in a longitudinal sectional view. The blood pump 1 has a substantially hollow cylindrical pump housing 1*a* having an inlet region 3 and an outlet region (not shown here) through which a fluid channel 2 leads from the inlet region 3 to the outlet region. The fluid channel 2 is bounded by a channel wall 2*b* and has a spherical section 2*a* toward the outlet region. The pump housing 1*a* has a flange-like broadened portion 1*c* in which the fluid channel 2 opens into a ring volute 12 downstream of the spherical region 2*a*. The outlet region (not shown here) is located in the ring volute 12.

A rotor 5 having a substantially cylindrical rotor body 5*a* is rotatably supported about an axis of rotation 7 in the fluid channel 2. For the mounting of the rotor 5, the blood pump 1 has a radial and axial mechanical ball cup bearing 8 that is arranged at the center of the spherical curvature of the spherical region 2*a*. Rotor magnets 5*c* are arranged in the middle region of the rotor body 5*a* and cooperate with a motor stator 6*b* arranged in the pump housing 1*a* and running around the rotor magnets 5*c* to drive the rotor 5. A magnetic rocker bearing 11 that cooperates with a bearing magnet 10 arranged adjacent to the rocker bearing 11 in the rotor body 5*a* is disposed toward the inlet region 3 in the pump housing 1*a* to stabilize tilt degrees of freedom of the rotor 5 in the front region of the blood pump 1 at the inlet side.

In the spherical region 2*a*, the rotor 5 has conveying elements 5*b* outwardly at the rotor body 5*a* in the spherical section that enable a conveying of the blood to be conveyed in a mixed radial and axial direction from the inlet region 3 into the ring volute 12. The ring volute 12 then changes a flow direction of the blood from the mixed radial and axial direction in a purely radial direction before the blood enters into the outlet region arranged in the ring volute 12. The conveying elements 5*b* further has a spherical outer contour corresponding to the spherical curvature of the spherical region 2*a* so that a rotational area results that is swept over by the conveying elements 5*b* on a rotation of the rotor 5. The curvature of this rotational area here corresponds to the curvature of the spherical region. The conveying elements 5*b* are further positioned at the rotor body 5*a* such that the center of the spherical rotational area and the center of the spherical section 2*a* substantially coincide with the pivot point of the bearing 8. This embodiment of the rotor 5 and the fluid channel 2 makes it possible that a minimal/minimum distance between the rotor 5 and the channel wall 2*b* also remains constant on a tilting of the rotor 5 and prevents the rotor 5 from contacting the channel wall 2*b* and the arising of damage to the rotor 5 or to the channel wall 2*b* or the impairment of the function of the blood pump 1 on the tilting of the rotor 5.

A position of the conveying elements 5*b* is shown in FIG. 6 with a maximum possible tilt of the rotor 5 about an axis orthogonal to the axis of rotation 7 by a small angle phi with respect to the axis of rotation 7. In this shown case, the front region of the rotor 5 at the inlet side nestles at the channel wall 2*b*. However, due to the spherical arrangement of the conveying elements 5*b* in the spherical region 2*a*, no contact of the rotor 5, in particular of the conveying elements 5*b*, with the channel wall 2*b* takes place. Damage is thus prevented by the design in accordance with the invention of the rotor 5 and the fluid channel 2 and an impairment of the function of the blood pump 1 caused thereby is avoided.

To enable a nestling over a larger region, both the rotor 5 and/or the channel wall 2*b* can be provided with a chamfer in this region. Hydraulically effective structures are furthermore possible in the region of the rotor-channel wall contact that bound a deflection of the rotor 5 or provide an additional hemocompatible support or that amplify or define the arising prerotation of the flow in the inlet region 3.

Figure 7:
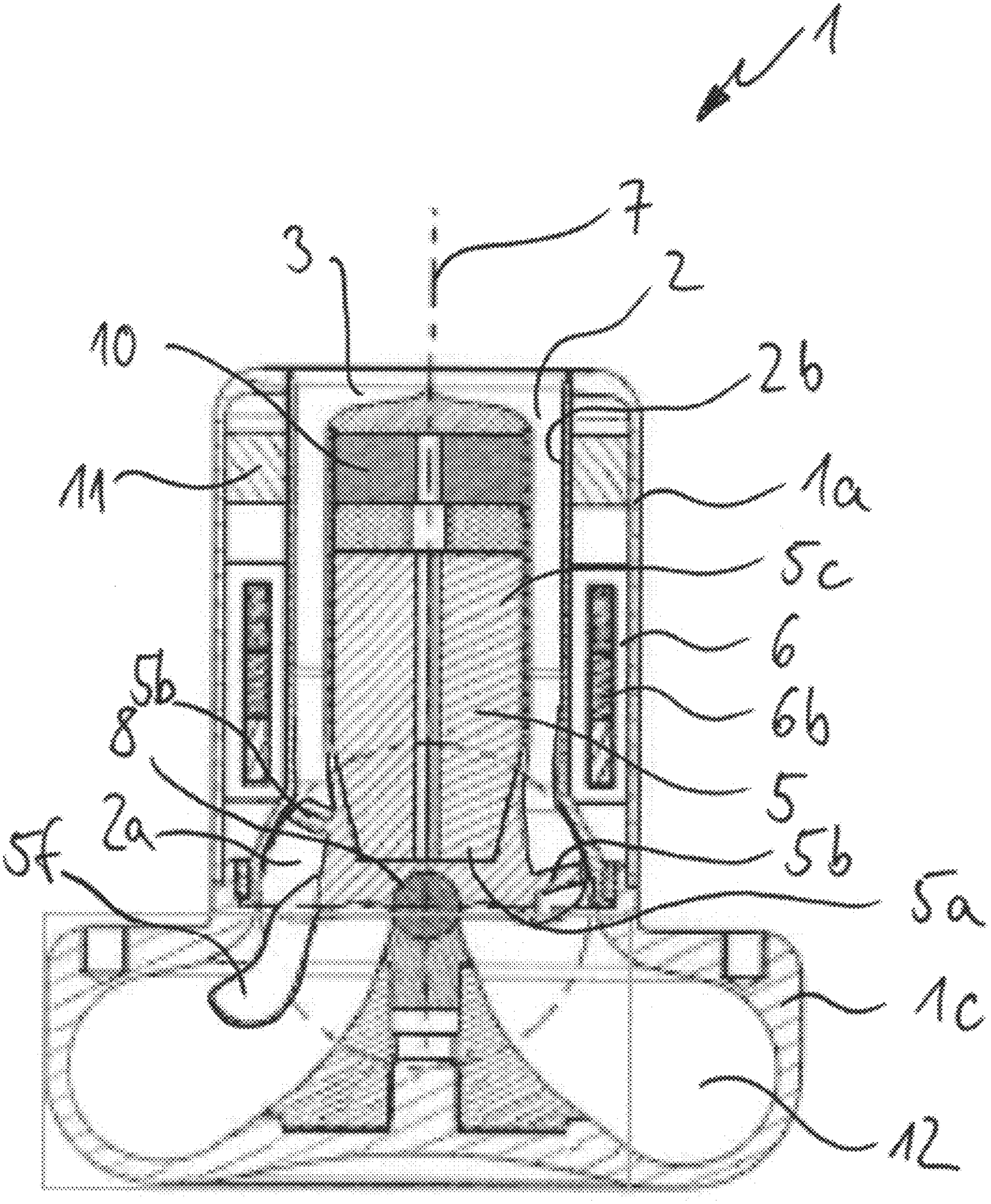
FIG. 7 is a blood pump mounted at the outlet side in accordance with a sixth embodiment.

FIG. 7 shows a blood pump 1 in accordance with a sixth embodiment in a longitudinal sectional view. The blood pump 1 is set up like the blood pump in FIGS. 5 and 6 and only differs by the presence of conveying elements 5*f* extended into the ring volute 12. The conveying elements 5*f* are, like the other conveying elements 5*b*, at least partially arranged in the spherical region 2*a* of the fluid channel 2 at an outer side of the rotor body 5*a*. The conveying elements 5*f* are furthermore arranged toward the volute 12 at the rotor body 5*a*. An outer contour of the conveying elements 5*f* is formed substantially spherically in the regions of the extended conveying elements 5*f* that are substantially located in the spherical region 2*a* so that these regions of the conveying elements 5*f* also sweep over a spherical rotational area on a rotation of the rotor 5, whereby no contact of the rotor 5 with the channel wall 2 takes place in the spherical section 2*a* on a tilting of the rotor 5. The extended conveying elements 5*f* improve a flow of the blood from the fluid channel 2 into the ring volute 12 and further to the outlet region (not shown here) and support the change of the direction of flow in the ring volute 12 from a mixed radial and axial direction to a purely radial direction of flow.

Figure 8:
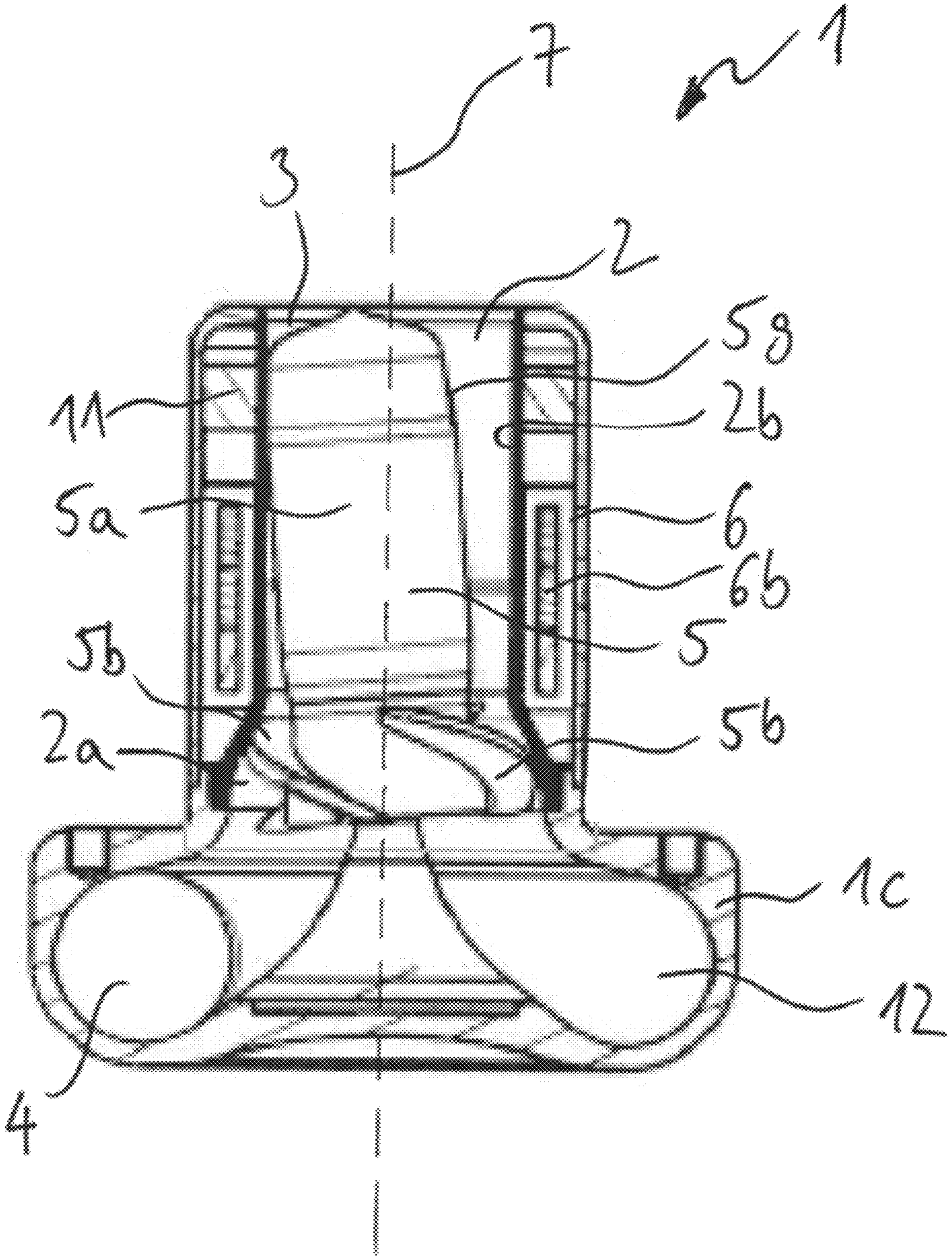
FIG. 8 is a blood pump mounted at the outlet side in accordance with a seventh embodiment.

FIG. 8 shows a blood pump 1 in accordance with a seventh embodiment in a longitudinal sectional view. The blood pump 1 in FIG. 8 is substantially set up like the blood pump of FIGS. 5 to 6 and only differs in the shape of the rotor body 5*a*. The rotor body 5*a* has a conical region 5*g* at the inlet side that tapers toward the inlet region and that is disposed in parallel with the channel wall 2*b* on a maximum possible tilt of the rotor 5. This improves a nestling of the rotor 5 in the region of the blood pump 1 at the inlet side and additionally reduces the risk of damage to the rotor 5 or to the channel wall 2*b* in the case of a tilting of the rotor 5.

Figure 9:
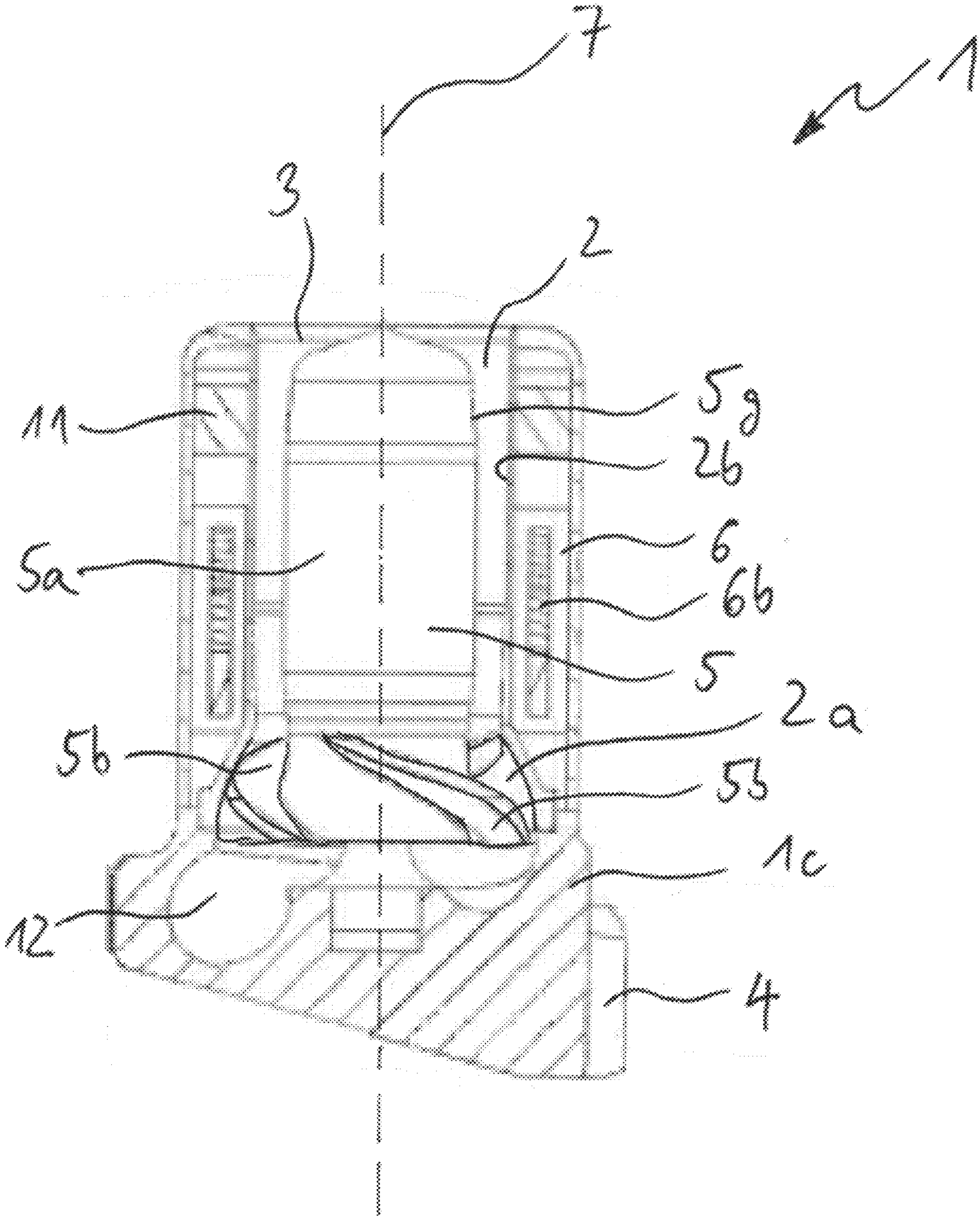
FIG. 9 is a blood pump mounted at the outlet side in accordance with an eighth embodiment.

FIG. 9 shows a blood pump 1 in accordance with an eighth embodiment in a longitudinal sectional view. The blood pump 1 in FIG. 8 is substantially set up like the blood pump in FIG. 8 and only differs in the shape of the volute 12. The blood pump 1 has a semi-axial volute 12 that conducts the blood both radially axially up to the outlet region 4 in a very compact manner. In the semi-axial volute 12, the conveyed blood is not subjected to any change or is only subjected to a change of the direction of flow very slowly from a mixed radial and axial direction to a purely radial direction of flow in the outlet region. This additionally improves the flow of the conveyed blood up to the outlet region 4 compared with a radial ring volume such as is shown, for example, in FIG. 8. The very slow change of direction of flow is typically advantageous for an optimal conversion of the radial and axial components of the flow of the fluid generated by operation of the rotor 5 into an increased change in fluid pressure. In particularly, it is advantageous to adapt the radial and axial components of the volute 12 to fit the direction of flow of the fluid coming from the spherical section 2*a* to the direction of flow into which the fluid is forced within the volute 12. The axial portion and the radial portion of the volute 12 in an inlet section of the volute are chosen such that a 3-dimensional volute flow vector at a radial angle does not deviate more than 30° from a 3-dimensional fluid flow vector of the fluid entering the volute at that radial angle when the rotor 5 is operated at a design point. The 3-dimensional volute flow vector is determined by a direction of flow that the volute forces the fluid into. This can, for example, be given by the surface normal of the fluid channel within the inlet section of the volute 12 at the radial angle. The radial angle is defined as an angle within a plane perpendicular to the axis of rotation 7 relative to a reference axis within that plane. The design point is defined by a chosen parameter or a chosen set of parameters characterizing an operation condition of the rotor 5 for which the rotor 5 is designed. In one example, the design point is defined by a number of RPM that the blood pump 1 is expected to be operated in on average. However, other definitions of the design point are also possible. Inlet sections of the volute 12 are all those parts of the volute that directly interface with the spherical section 2*a* of the blood pump 1. The relationship between volute flow vector and fluid flow vector will be explained in the following in more detail with reference to FIG. 10*a* and FIG. 10*b*.

Figure 10A:
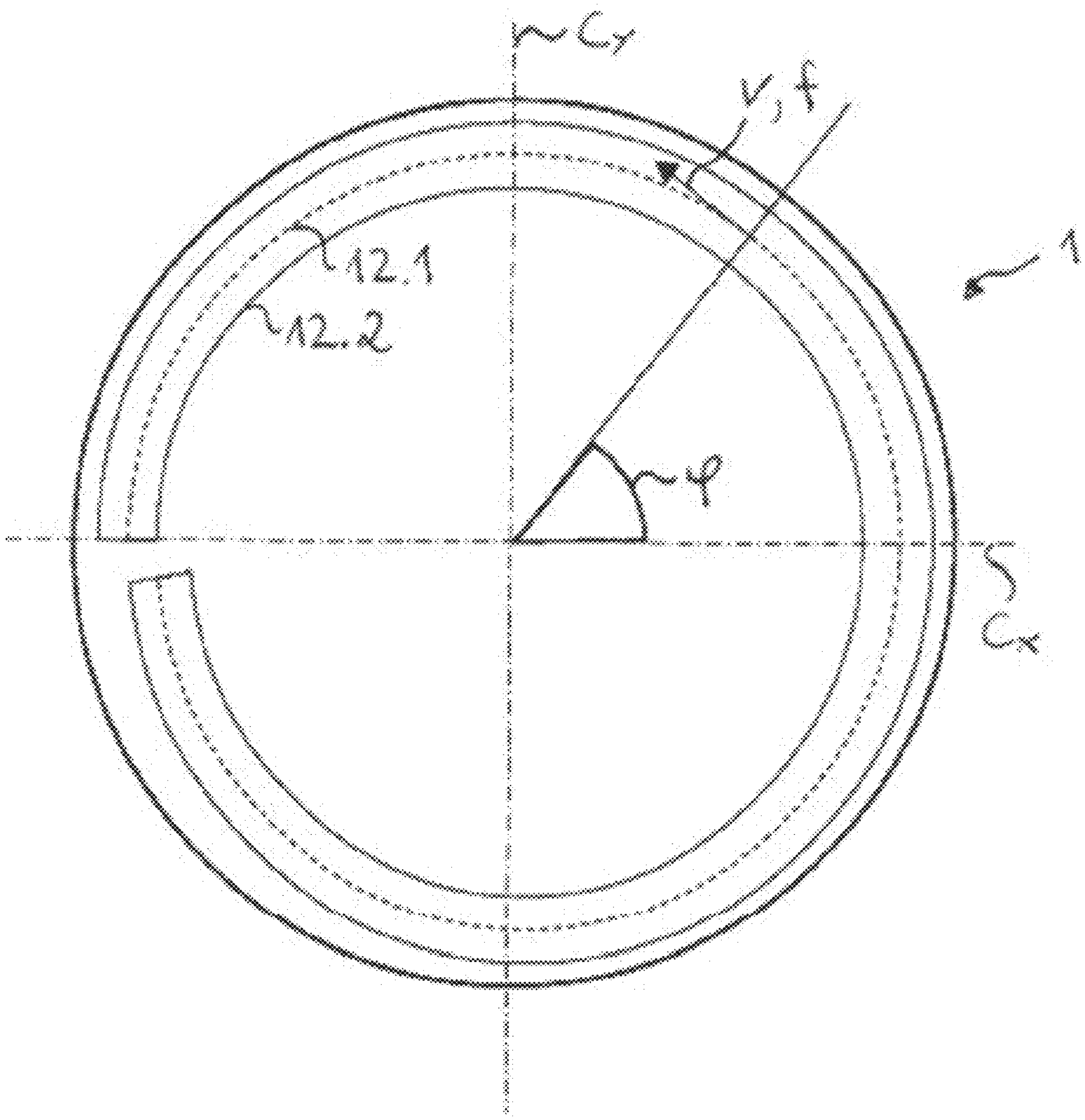
FIG. 10*a* is a cross sectional view of the blood pump in accordance with the eighth embodiment.
Figure 10B:
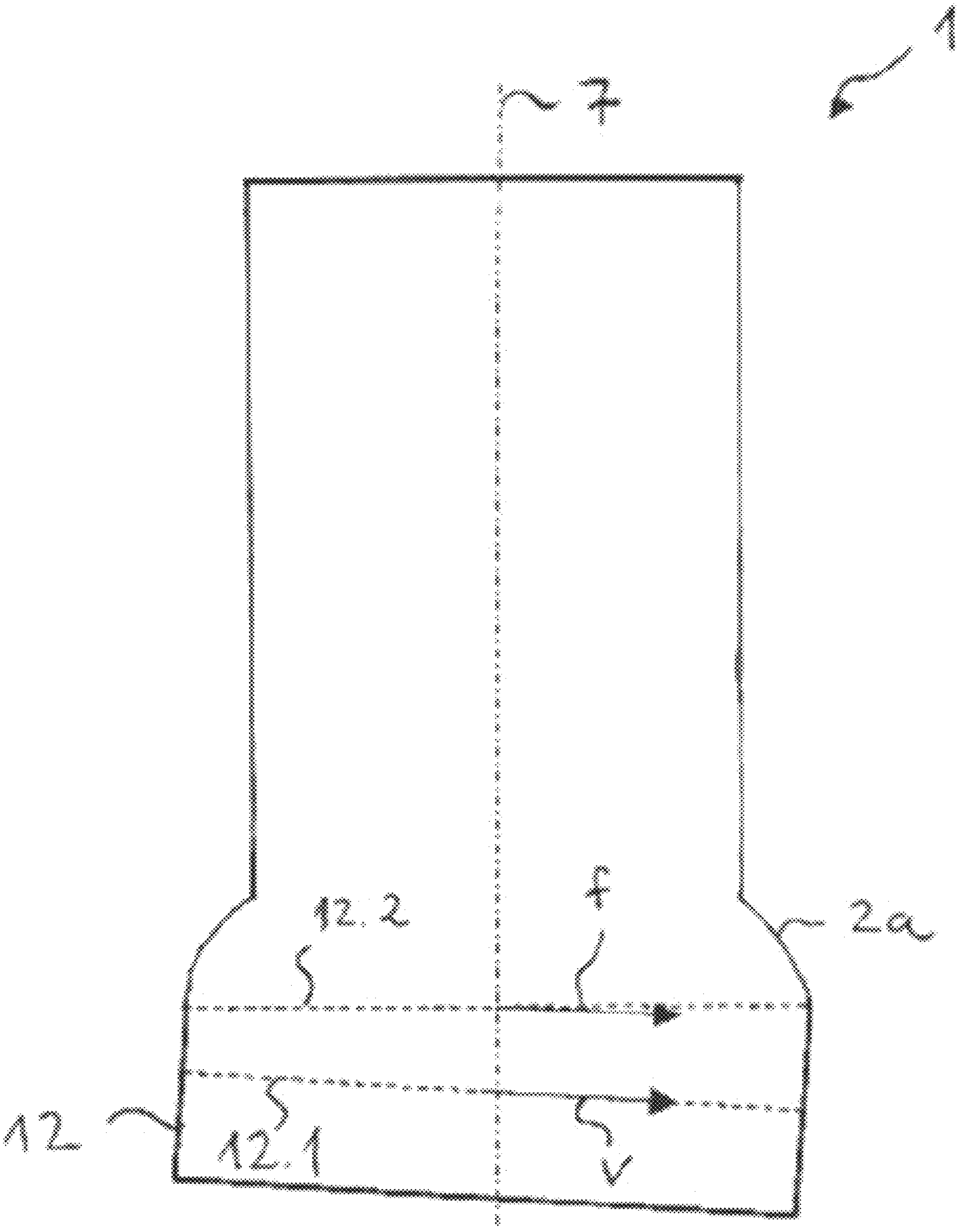
FIG. 10*b* is a side view of the blood pump in accordance with the eighth embodiment.

FIG. 10*a* shows a simplified cross-sectional view of the blood pump 1 of FIG. 9 perpendicular to the axis of rotation 7. The cross-sectional view shows an interface between the volute 12 and the spherical section 2*a*. FIG. 10*b* shows a simplified side view of the blood pump 1 of FIG. 9.

The cross-sectional view shows a volute inlet 12.2 of the volute 12 that forms an opening through which fluid can flow from the spherical section 2*a* into the volute 12. A solid line indicates the volute inlet 12.2, which has the form of a channel expanding radially over an angle ϕ in the plane of the cross-section. The width of the channel in this plane is constant in the shown example, however, can expand with an increasing angle ϕ in the counter-clockwise direction. A dashed line indicates a projection of the center line 12.1 of the volute 12 in the plane of the cross-section. Please note that the actual center line changes its position along the pump axis (downward direction in FIG. 10*b*) over the angle ϕ. The radial angle ϕ is indicated for an arbitrarily defined coordinate system given by axes Cx and Cy. For the radial angle ϕ, a 3-dimensional volute flow vector v is indicated that corresponds to the surface normal of the fluid channel within the volute 12 facing downstream from the rotor 5. The same arrow that is indicating the 3-dimensional volute flow vector v also indicates the 3-dimensional fluid flow vector f, which are approximately identical with respect to their components lying within the plane spanned by the coordinate axes Cx and Cy. While the projection of center line 12.1 is shown as a circle centered in the volute inlet, the actual centerline projection may wander towards the outer edge of the volute inlet indicated by the solid line with an increasing angle ϕ in the counter-clockwise direction. This is equivalent with the view shown in FIG. 9, where the center line at the right side of the volute as shown in FIG. 9 is close to the center of the volute inlet, whereas the center lien is axially further downward and to the left of the volute inlet.

In the side view of FIG. 10*b*, also those components of vector v and vector f are visible which are parallel to the axis of rotation 7. In the example of FIGS. 10*a* and 10*b*, the 3-dimensional fluid flow vector f of the fluid entering the volute 12 at the radial angle ϕ is approximately identical to the 3-dimensional volute flow vector v. However, in other examples, there is can be deviation of up to 30° between those vectors. In the example, the comparison of vector v and f is shown for only one radial angle. However, the condition is fulfilled for all radial angles. Also, in the example of FIG. 10*a* and FIG. 10*b*, only a single fluid flow vector f is shown. However, in some examples, the fluid flow vector f is different along the opening 12.2 for the same radial angle. Nevertheless, each of those vectors should not deviate from the volute flow vector by more than 30°.

As is visible in FIG. 10*a* and FIG. 10*b*, the volute 12 expands continuously radially and axially towards the fluid outlet 4 downstream from the rotor 5. In other words, the volute 12 forms a spiral around the axis of rotation 7, which expands along the axis of rotation 7 and whose radius is continuously increasing downstream from the rotor 5. In some examples, the expansion only takes place downstream from the rotor 5. In other examples, in addition, the volute 12 has a diameter that continuously increases downstream from the rotor 5. In yet other examples, additionally or alternatively, a pitch of the volute in axial direction increases continuously downstream from the rotor 5. The different configurations of the volute just described typically lead to a reduction in flow separation, backflow and the formation of uncontrolled vortex streets, which reduces blood-damaging and thrombogenic influences.

Figure 11:
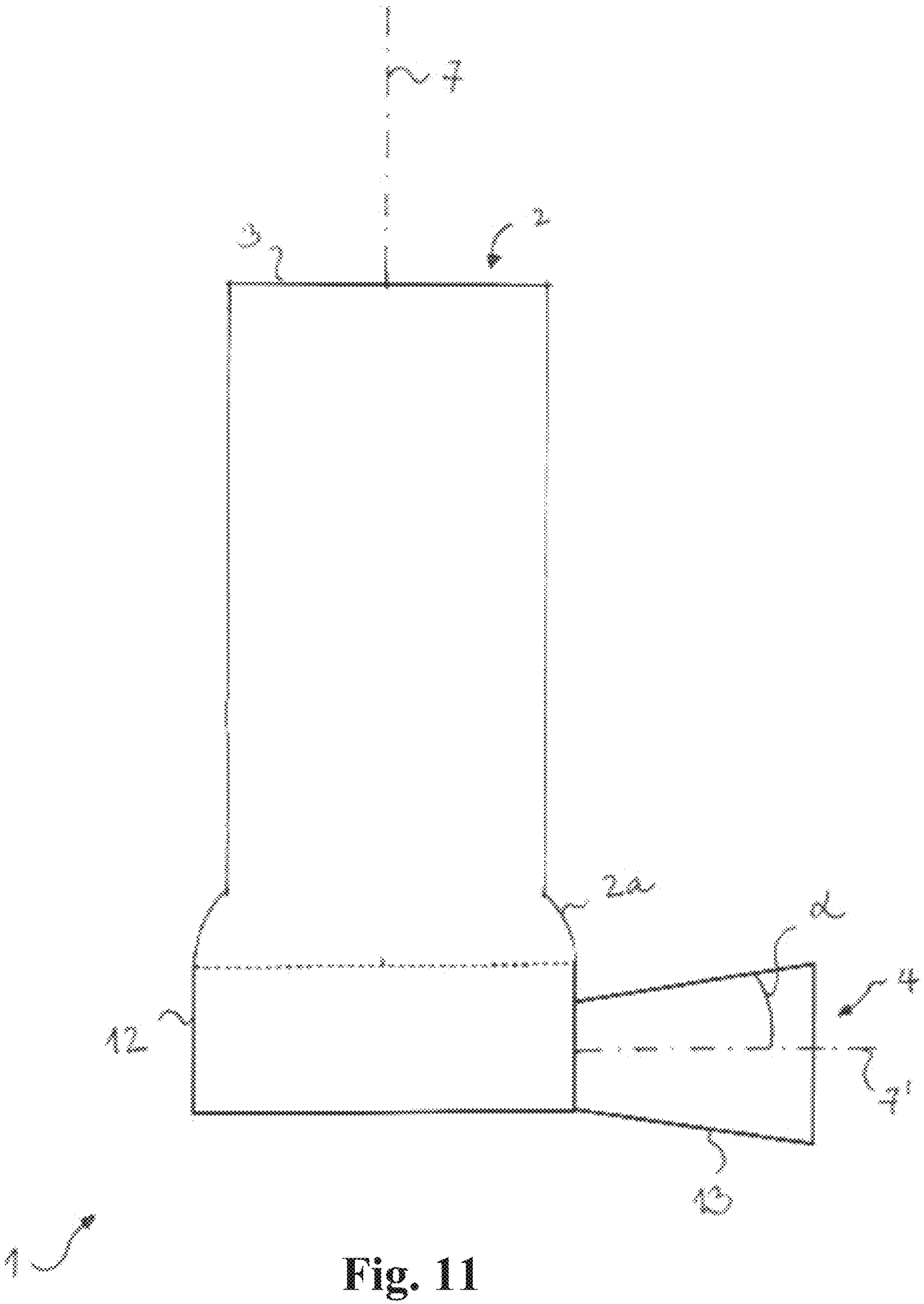
FIG. 11 is a blood pump mounted at the outlet side in accordance with a ninth embodiment.

FIG. 11 shows a blood pump 1 in accordance with a ninth embodiment. The blood pump 1 comprises a fluid channel 2 with an inlet region 3 and a spherical section similar to the blood pumps according to the previously described embodiments. The fluid channel 2 extends primarily along an axis of rotation 7. Furthermore, the blood pump 1 comprises a volute 12 in proximity to a fluid outlet 4, wherein an end piece 13 is mounted in fluid connection with the fluid outlet 4 of the volute 12. The end piece 13 comprises a diffuser with an opening angle in a range between 5° and 20°. The opening angle of the diffuser is given with respect to a center line 7' of the fluid channel 2 within the diffuser. However, the diffuser can alternatively also be present in the volute 12 itself.

Figure 12:
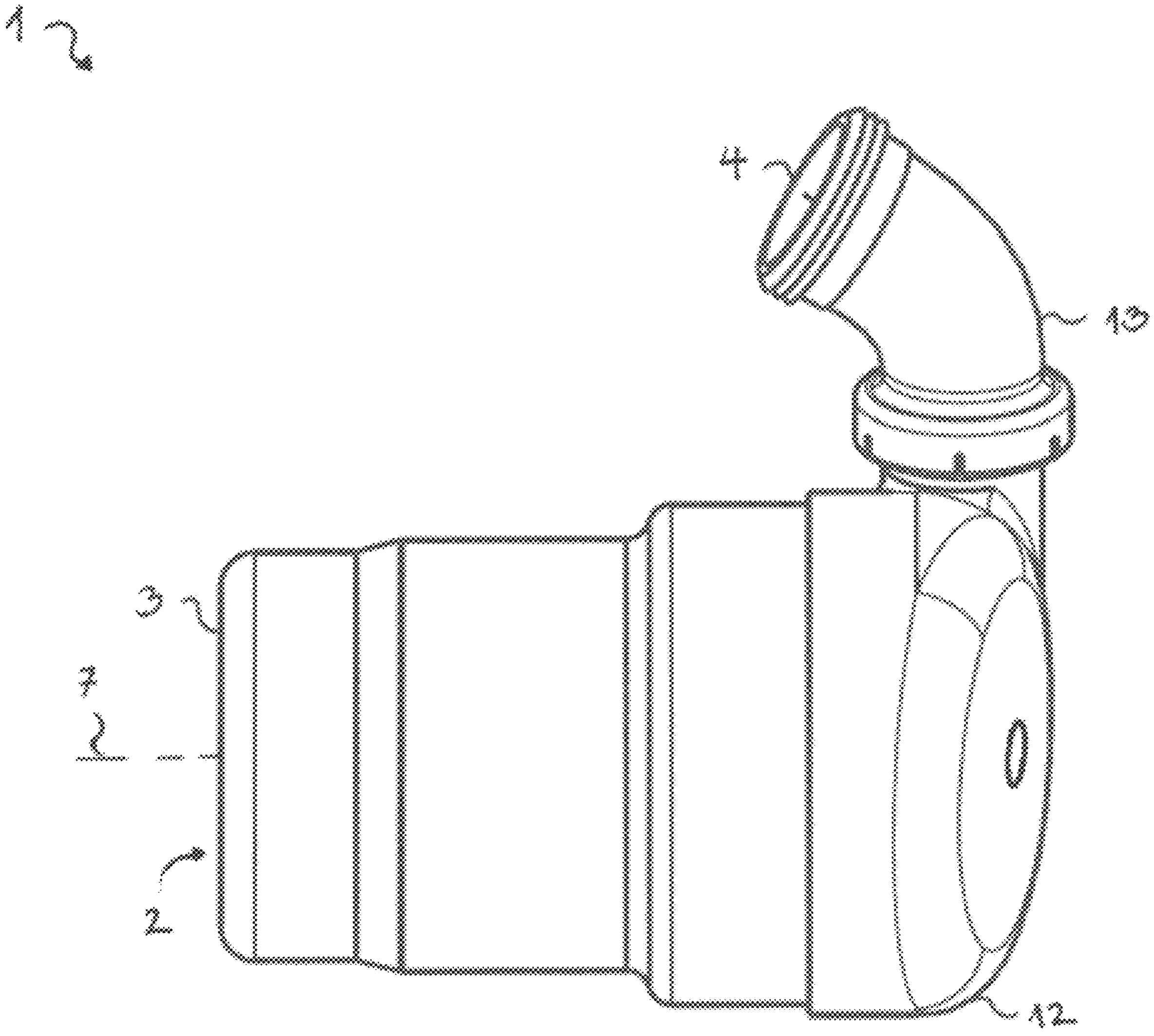
FIG. 12 is a blood pump mounted at the outlet side in accordance with a tenth embodiment.

FIG. 12 shows a blood pump 1 in accordance with a tenth embodiment. The blood pump 1 comprises a fluid channel 2 with an inlet region 3 and a spherical section similar to the blood pumps according to the previously described embodiments. The fluid channel 2 extends primarily along an axis of rotation 7. Furthermore, the blood pump 1 comprises a volute 12 in proximity to a fluid outlet 4, wherein an end piece 13 is mounted in fluid connection with the fluid outlet 4 of the volute 12. The end piece 13 is pivotable around an axis perpendicular to the axis of rotation 7 and, as a result, allows to adapt a position of the fluid outlet 4 of the fluid channel 2 according to the needs of the patient.

The illustrations of the embodiments described herein are intended to provide a general understanding of the structure of the various embodiments. The illustrations are not intended to serve as a complete description of all of the elements and features of apparatus and systems that utilize the structures or methods described herein. Many other embodiments may be apparent to those of skill in the art upon reviewing the disclosure. Other embodiments may be utilized and derived from the disclosure, such that structural and logical substitutions and changes may be made without departing from the scope of the disclosure. Additionally, the illustrations are merely representational and may not be drawn to scale. Certain proportions within the illustrations may be exaggerated, while other proportions may be minimized. Accordingly, the disclosure and the figures are to be regarded as illustrative rather than restrictive.

One or more embodiments of the disclosure may be referred to herein, individually and/or collectively, by the term "invention" merely for convenience and without intending to voluntarily limit the scope of this application to any particular invention or inventive concept. Moreover, although specific embodiments have been illustrated and described herein, it should be appreciated that any subsequent arrangement designed to achieve the same or similar purpose may be substituted for the specific embodiments shown. This disclosure is intended to cover any and all subsequent adaptations or variations of various embodiments. Combinations of the above embodiments, and other embodiments not specifically described herein, will be apparent to those of skill in the art upon reviewing the description.

The above disclosed subject matter is to be considered illustrative, and not restrictive, and the appended claims are intended to cover all such modifications, enhancements, and other embodiments, which fall within the true spirit and scope of the present invention. Thus, to the maximum extent allowed by law, the scope of the present invention is to be determined by the broadest permissible interpretation of the following claims and their equivalents, and shall not be restricted or limited by the foregoing detailed description. While various embodiments of the invention have been described, it will be apparent to those of ordinary skill in the art that many more embodiments and implementations are possible within the scope of the invention. Accordingly, the invention is not to be restricted except in light of the attached claims and their equivalents.

The invention claimed is:

1. An axial fluid pump for conveying blood as a fluid comprising:
- a fluid channel for conveying blood, that is bounded by a channel wall and extending axially between an inlet region and an outlet region, the fluid channel comprising a spherical section;
- a rotor disposed in the fluid channel and extending from the inlet region towards the outlet region, the rotor is-rotatably mounted about a pivot point of a bearing by a mechanical, hydrodynamic and/or hydrostatic, axial and radial bearing, wherein the rotor comprises:
  - a rotor body; and
  - a conveying element disposed within the spherical section of the fluid channel and that is configured to generate a substantially spherical rotational area of the rotor; and
- wherein a spherical center of the spherical section of the fluid channel and a spherical center of the substantially spherical rotational area coincide with the pivot point such that a minimum distance between the rotor and the channel wall is maintained in the spherical section during a tilting of the rotor.

2. The fluid pump of claim 1, wherein the bearing comprises a ball cup bearing or a pin bearing.

3. The fluid pump of claim 1, wherein the bearing comprises a passively magnetic bearing, with the passively magnetic bearing being formed as a rocker bearing for returning a tilt of the rotor or configured to axially preload the rotor with respect to the fluid channel.

4. The fluid pump of claim 1, further comprising:
- a motor stator disposed at the channel wall of the flow channel; and
- a motor magnet integrated in the rotor body or in the conveying element, wherein a passively magnetic rocker bearing is implemented by a magnetic attraction or repulsion between the motor stator and the motor magnet.

5. The fluid pump of claim 1, wherein the fluid channel is shaped as conical, tapering toward the bearing on a side disposed opposite the bearing, further wherein a taper angle of the fluid channel corresponds to a maximum tilt angle of the rotor within the fluid channel.

6. The fluid pump of claim 5, wherein the rotor body is shaped as conical, tapering in a direction away from the bearing on a side disposed opposite the bearing, further wherein a taper angle of the rotor body corresponds to a maximum tilt angle of the rotor within the fluid channel.

7. The fluid channel of claim 1, wherein the bearing comprises a hydrostatic or hydrodynamic auxiliary bearing disposed in the fluid channel to bound the tilt of the rotor.

8. The fluid pump of claim 7, wherein the hydrostatic or hydrodynamic auxiliary bearing is formed by guide blades arranged at the channel wall.

9. The fluid pump of claim 1, wherein hydrodynamically active elements are disposed on a side of the fluid channel opposite the bearing at the channel wall or at the rotor to improve a nestling of the rotor to the channel wall upon the tilting of the rotor.

10. The fluid pump of claim 1, wherein the fluid channel further comprises:
- a fluid inlet; and
- a fluid outlet, wherein the bearing is disposed at the fluid inlet, at the fluid outlet, or at a center of the fluid channel.

11. The fluid pump of claim 10, wherein the fluid outlet comprises an axial, tangential, or axially tangentially mixed fluid outlet.

12. The fluid pump of claim 10, wherein the fluid pump has a volute in the region of the fluid outlet, wherein the volute comprises a ring volute, a logarithmic volute, or a volute having an axial portion.

13. The fluid pump of claim 1, wherein the bearing comprises a mechanical bearing, wherein the mechanical bearing comprises a hemocompatible, hard, wear resistant, or thermally conductive material;
- further wherein the material comprises
  - a ceramic material, a mixed ceramic material, crystalline material, or tantalum nitride; and
- a sliding layer.

14. The fluid pump of claim 1, wherein the bearing comprises a magnetic bearing and the motor stator is axially displaceable so that a preload of the rotor in the bearing can be set.

15. The fluid pump of claim 1, wherein the fluid channel comprises:

a volute, in proximity to a fluid outlet, configured to expand in axial direction and in radial direction.

16. The fluid pump of claim 1, wherein the fluid channel comprises:

a volute, in proximity to a fluid outlet, having an axial and a radial portion, wherein the axial portion and the radial portion of the volute in an inlet section of the volute allow a 3-dimensional volute flow vector (v) at a radial angle that does not deviate more than 30° from a 3-dimensional fluid flow vector (f) of the fluid entering the volute at that radial angle when the rotor is operated at a design point, further wherein the 3-dimensional volute flow vector (v) is given by the surface normal of the fluid channel within the inlet section of the volute at the radial angle.

17. A fluid pump of claim 1, wherein the fluid channel comprises a diffuser with an opening angle between 5° and 20°, at a fluid outlet of the fluid channel.

18. A fluid pump of claim 1, wherein the fluid channel comprises a fluid outlet that is pivotable.

* * * * *